(12) United States Patent
Madit

(10) Patent No.: US 8,795,720 B2
(45) Date of Patent: Aug. 5, 2014

(54) LIQUID FILLED DELIVERY SYSTEM

(75) Inventor: Nicolas Madit, Brunstatt (FR)

(73) Assignee: Capsugel Belgium NV, Bornem (BE)

( * ) Notice: Subject to any disclaimer, the term of this patent is extended or adjusted under 35 U.S.C. 154(b) by 1220 days.

(21) Appl. No.: 11/511,808

(22) Filed: Aug. 29, 2006

(65) Prior Publication Data

US 2007/0059355 A1 Mar. 15, 2007

(30) Foreign Application Priority Data

Sep. 9, 2005 (EP) ..................................... 05291875

(51) Int. Cl.
*A61K 9/66* (2006.01)
*A61K 9/48* (2006.01)

(52) U.S. Cl.
USPC .......................................... 424/455; 424/451

(58) Field of Classification Search
None
See application file for complete search history.

(56) References Cited

U.S. PATENT DOCUMENTS

| | | | |
|---|---|---|---|
| 5,456,746 A | 10/1995 | Kokubun et al. | |
| 5,626,871 A | 5/1997 | Makino et al. | |
| 6,214,378 B1 | 4/2001 | Tanida et al. | |
| 6,238,696 B1 | 5/2001 | Wang | |
| 2003/0045563 A1 | 3/2003 | Gao et al. | |
| 2003/0050344 A1 | 3/2003 | Garavani et al. | |
| 2005/0079164 A1 | 4/2005 | Fantuzzi et al. | |
| 2006/0246127 A1* | 11/2006 | Freier | ........................... 424/451 |

FOREIGN PATENT DOCUMENTS

| | | | | |
|---|---|---|---|---|
| JP | A-H10-152431 | 6/1998 | | |
| JP | A-2002-525412 | 8/2002 | | |
| JP | A-2005-154301 | 6/2005 | | |
| WO | WO 93/25193 | 12/1993 | | |
| WO | WO 00/18835 | 4/2000 | | |
| WO | WO 02/49637 A | 6/2002 | | |
| WO | WO2004/062650 | * | 7/2004 | ............... A61K 9/48 |

OTHER PUBLICATIONS

Bertelli, A, L-carnitine and coenzyme Q10 protective action against ischemia and reperfusion of working rat heart, 1992, Drugs Exp Clin Res, 18(10), pp. 431-436 (Abstract only, 1 page).*
Nagata, Advantages od HPMC Capsules: A New Generation, 2002, Drug Development and Delivery, vol. 2, No. 2, pp. 1-5.*
Office Action dated May 29, 2012 from Japanese Patent Application No. 2008-529706.

* cited by examiner

*Primary Examiner* — Trevor Love
(74) *Attorney, Agent, or Firm* — Finnegan, Henderson, Farabow, Garrett & Dunner

(57) ABSTRACT

The present invention provides a delivery system comprising: (a) a container which is a formed body obtained from a film forming composition comprising at least one polysaccharide or polysaccharide derivative; (b) a liquid fill comprising a matrix composition of at least one solvent which is both polar and hygroscopic or a mixture of solvents each of which is both polar and hygroscopic; and (c) an active agent or a mixture of active agents wherein the active agent is soluble in said polar and hygroscopic solvent or mixture of polar and hygroscopic solvents, and a process for the preparation of said delivery system.

7 Claims, No Drawings

LIQUID FILLED DELIVERY SYSTEM

FIELD OF THE INVENTION

The present invention relates to a delivery system comprising at least a container that is a formed body obtained from a film forming composition; a liquid fill comprising a matrix composition of at least one solvent which is both polar and hygroscopic or a mixture of two or more of such solvents; and an active agent or mixture thereof soluble in the matrix composition. The matrix composition and the active agent considered together are preferably clear and/or transparent and/or in a liquid form. The container is preferably a capsule. The present invention relates also to a process for the preparation of a delivery system comprising at least a container that is a formed body obtained from a film forming composition, a liquid fill comprising a matrix composition of at least one polar and hygroscopic solvent or a mixture thereof and an active agent or mixture thereof soluble in the matrix composition. Further the present invention relates to the use of a container for delivering active agent(s). Active agents can be herbs, foodstuffs, pharmaceuticals, cosmetic products, or flavouring agents.

BACKGROUND OF THE INVENTION

U.S. Pat. No. 4,727,109 relates to a pharmaceutical preparation having an active substance of low solubility in water and gastric juices. The active substance is dissolved in a carrier system that consists of a hydrophobic component such as vegetal oils, a hydrophilic component such as polyethylene glycol and a solubilizer such as triethylcitrate. The pharmaceutical preparation is contained in a hard gelatin capsule.

EP 0127297 relates to a vitamin or mineral composition comprising a vitamin or a mineral and at least a polyoxyethylene sorbitan ester. Optionally the composition may contain a non-toxic alcohol or other diluents such as vegetal oils and derivatives. The composition is contained in a solid unit dosage form such as a hard shell capsule or a soft elastic capsule. The capsule is preferably made of gelatin.

U.S. Pat. No. 6,056,971 relates to a method for enhancing the dissolution and bioavailability properties of a dietary supplement that can be e.g. Coenzyme Q 10 (ubiquinone). The Coenzyme Q 10 is contained in a unit dosage form a gelatin capsule.

Capsules are widely used in the pharmaceutical industry as well as in the health food supplement market. The main usage thereof is as a dosage form for solid, semi-solid, liquid, pellet or herbal preparations. A primary objective of these dosage forms is to have a good disintegration after being administrated in order to enable a fast dissolution of the active substances in the appropriate digestive organ. Any delay of the disintegration would consequently retard or even reduce the effect of the drug. Consequently, this disintegration characteristic has to remain unchanged over time when finished products are stored prior to use.

The traditional material for forming the capsule shell is gelatin, because it has correct and quite ideal properties. Conventional hard capsules are made with gelatin by dip moulding processes. For the industrial manufacture of pharmaceutical capsules gelatin is most preferred for its gelling, film forming and surface active properties. Traditionally, gelatin is produced by extraction from collagen containing mammalian tissues, particularly such as pig skin and bovine bone.

Gelatin has some disadvantages, however, which make it necessary to have other capsule shell materials available. A major unfavourable aspect is the animal origin of gelatin. Other disadvantages are the inconveniences of relatively high water content (10-17%) and the loss of elasticity with decreasing water content. Furthermore gelatin capsules are sensitive to heat and humidity which affect the usability of the product. In particular soft gelatin capsules are known to aggregate under hot and humid conditions. Under dry conditions gelatin films may induce static charge build up affecting later processing.

It has long been recognized that gelatin capsules become brittle when they lose some of their moisture content. Water acts as a plasticizer in gelatin films and when the level falls below about 10%, they become very brittle. On the other hand when the water content increases the capsule shell can weaken and finally leakage will occur.

The formulation of drugs into soft gelatin capsules has gained popularity throughout the past decade due to the many advantages of this dosage form. The bioavailability of hydrophobic drugs can be significantly increased when formulated into soft gelatin capsules. Many problems associated with tableting, including poor compaction and lack of content or weight uniformity, can be eliminated when a drug is incorporated into this dosage form.

Soft gelatin capsules generally contain the medicament dissolved or dispersed in oils or hydrophilic liquids (i.e. fill liquid). The inherent flexibility of the soft gelatin capsule is due to the presence of plasticizers and residual moisture in the capsule shell. A disadvantage of soft gelatin capsules is that the atmospheric moisture may permeate into the capsule shell or into the fill. Volatile components in soft gelatin capsules may escape into the atmosphere. These liquid mixtures are very often dispersions which show a reduced bioavailability in particular in the gastrointestinal tract. In order to overcome these problems it has been suggested to use more complex solvent systems in gelatin capsules.

Other disadvantages are the problems related to capsule shell/contents interactions or unacceptable taste and smell.

Therefore, there is a need to provide containers in line with customer dietary (e.g. vegetarian) and religious orientations and at the same time to enhance bioavailability of low soluble substances by providing an appropriate solvent that, among its high solubilising capability, is also compatible with non-animal based containers and low soluble substances.

The object of the present invention is, therefore, the provision of an improved delivery system comprising a container and a liquid fill which overcomes the above mentioned drawbacks of the prior art compositions.

This object is solved according to a delivery system, a process for preparation thereof and uses according to the independent claims.

Further advantageous features, aspects and details of the invention are evident from the dependent claims, and the description. The claims are to be understood as a first non-limiting approach to define the invention in general terms.

SUMMARY OF THE INVENTION

The invention provides a delivery system comprising:
(a) a container which is a formed body obtained from a film forming composition comprising at least one polysaccharide or polysaccharide derivative;
(b) a liquid fill comprising a matrix composition comprising of at least one solvent which is both polar and hygroscopic or a mixture of solvents each of which is both polar and hygroscopic; and (c) an active agent or a mixture of active agents wherein the active agent is soluble in said polar and hygroscopic solvent or mixture of polar and hygroscopic solvents.

It is one object of the invention to provide a delivery system which is able to provide a container with a liquid fill and wherein the active ingredient is solubilized in the polar and hygroscopic solvent(s).

A further object of the present invention is to provide a delivery system using a simple solvent system preferably only one or two different polar and hygroscopic solvent(s).

Liquid filled containers according to the present invention improve the performance of the active agent contained therein by improving the bioavailability of the active agent.

The delivery system of the present invention provides improved dissolution properties and improved content uniformity of low dose compounds. Further container presents low oxygen permeability in comparison to soft gelatine capsules.

The container of the present delivery system can be a capsule, casing, bag, bowl, box, can, canister, package, packet, receptacle, sac, sack, vessel, and vial. Preferably the container is a hard or soft capsule. More preferably the container is a hard capsule.

A delivery system according to the present invention can be manufactured easily by using conventional equipment.

DETAILED DESCRIPTION OF THE INVENTION

The bioavailability of an active agent can be affected by the compatibility of the active agent with the excipient, the solvent, the carrier or the wall of the container. The present invention provides a liquid fill comprising a matrix composition and a container with high compatibility with the active agent. Although, the container has a moisture content of about 3% to 16% and preferably 4% to 6%, it has been surprisingly found that a hygroscopic matrix composition of the present invention does not act as a moisture sink and that no moisture migrates from the container wall into the liquid fill or from the liquid fill into the container wall. Furtheron it has been surprisingly found that the polar and hygroscopic solvent or the mixtures thereof do not migrate into the container wall or interact with it.

The container is a formed body obtained from a film forming composition comprising at least one polysaccharide or polysaccharide derivative. The polysaccharide or derivative thereof can be cellulose, cellulose derivatives, starch, modified starches, pullulan, dextran or the like and mixtures of any of the foregoing.

Suitable cellulose derivatives are selected from the group consisting of alkylcelluloses, hydroxyalkylcelluloses, hydroxyalkylalkylcelluloses, carboxyalkylcelluloses, and carboxyalkyl-alkylcelluloses including, but not limited to, members selected from the group consisting of methyl cellulose, ethyl cellulose, hydroxymethylcellulose, hydroxyethyl cellulose, hydroxyethylethyl cellulose, hydroxypropyl cellulose, hydroxypropylmethyl cellulose (HPMC), hydroxyethylmethyl cellulose, hydroxybutylmethylcellulose, cellulose acetylphtalate (CAP), sodium carboxymethyl cellulose and mixtures of any of the foregoing. Especially preferred is hydroxpropylmethyl cellulose (HPMC).

Additional cellulose derivatives include cellulose ethers. Suitable cellulose ethers are selected from the group consisting of alkyl- and/or hydroxyalkyl substituted cellulose ether with 1 to 4 carbon atoms in the alkyl chains, and are preferably selected from the group consisting of methyl cellulose ether, hydroxyethyl cellulose ether, hydroxypropyl cellulose ether, hydroxyethylmethyl cellulose ether, hydroxyethylethyl cellulose ether, hydroxypropylmethyl cellulose ether or the like and mixtures of any of the foregoing. Especially preferred is hydroxpropylmethyl cellulose ether.

A particular group of cellulose derivatives are those selected from the group consisting of methyl cellulose, ethyl cellulose, hydroxymethyl cellulose, hydroxyethyl cellulose, hydroxyethylethyl cellulose, hydroxypropyl cellulose, hydroxypropylmethyl cellulose (HPMC), hydroxyethylmethyl cellulose, hydroxybutylmethyl cellulose, cellulose acetylphthalate (CAP), sodium carboxymethyl cellulose, methyl cellulose ether, hydroxyethyl cellulose ether, hydroxypropyl cellulose ether, hydroxyethylmethyl cellulose ether, hydroxyethylethyl cellulose ether, and hydroxypropylmethyl cellulose ether.

Beside starch, modified starches can be used, such as starch ethers and oxidized starches, carboxymethyl starches, hydroxyalkylated starches, and succinated starches, more particularly hydroxypropylated starch (HPS) or hydroxyethylated starch (HES) or mixtures thereof can be used as a film forming material in the film forming composition for obtaining the container according to the present invention. Modified starches disclosed in U.S. Pat. No. 6,635,275 B1 are suitable for the present invention. Most preferred modified starch is HPS.

In one particular embodiment the container is a formed body obtained from a film forming composition comprising at least one polysaccharide or polysaccharide derivative or mixture thereof from about 90% to 99% by weight of the final container. The viscosity of the polysaccharide, polysaccharide derivative or mixture thereof is from 3 to 15 cps in 2% aqueous solution at 20° C., preferably from 5 to 10 cps, and more preferably 6 cps.

In one particular embodiment the container is a formed body obtained from a film forming composition comprising at least one polysaccharide or polysaccharide derivative or mixture thereof from about 5% to about 40% of the aqueous solution. Most preferred the container is a formed body obtained from about 17% of the aqueous solution.

In a preferred embodiment according to the present invention the container is a hard HPMC capsule. The capsule may be a two-piece hard capsule, which can be produced by dipping method or produced by injection-moulding method. The capsule can be a one compartment dosage form as well as a multiple compartment dosage form. Suitable methods for making such two-piece capsules include those methods found in the art. For example, a two-piece capsule may be made by the dipping method described in "Pharmaceutical Capsules" second edition, from Fridrun Podczeck and Brian E Jones et al, page 80-84.

In a further preferred embodiment according to the present invention the container is a soft capsule, which can be produced by any methods found in the art. For example, a soft capsule may be obtained using the rotary die process patented by Scherer in 1993 and described in the "Encyclopedia of pharmaceutical technology", second edition, vol 1, from Swarbrick J. pages 320-323.

The film forming composition for obtaining the container of the present invention may optionally comprise a suitable gelling agent selected from known gelling agents with the proviso that such gelling agent improves the gelling capability of the capsule and does not interact with the liquid fill comprising the matrix composition and/or the active agent(s). Examples of suitable gelling agents include alginic acid, sodium alginate, potassium alginate, calcium alginate, agar, carrageenan, carob gum, and gellan gum. Most preferred gelling agent is gellan gum.

The capsule may optionally be coated with a suitable coating agent such as a member selected from the group consisting of cellulose acetate phthalate, polyvinyl acetate phthalate, methacrylic acid gelatines, hypromellose phthalate, hydroxypropylmethyl cellulose phthalate, hydroxyalkyl methyl cellulose phthalates, hydroxypropyl methylcellulose acetate succinate and mixtures thereof to provide e.g. enteric properties.

In a further embodiment of the invention, the capsules can additionally be sealed using means known in the art such as banding or liquid sealing technology. Examples of suitable sealing techniques are those described in WO 01/08631, U.S. Pat. No. 2,962,851, and in "Pharmaceutical capsules", second edition, from Fridrun Podczeck and Brian E Jones et al, pages 182-184. More preferably the capsules are sealed using a hydro alcoholic solution for example, as described in WO 01/08631.

The liquid fill according to the present invention comprises a matrix composition at least one or more solvents, each of which is both polar and hygroscopic.

Preferably the matrix composition comprises at least one solvent which is both polar and hygroscopic in an amount of from 20% to 80% by weight based on the liquid fill composition and more preferably the matrix composition contains at least one solvent from 40% to 60% by weight based on the liquid fill composition.

It is most preferred that the liquid fill is a solution and not a dispersion. The term liquid refers to the physical condition at room temperature (20° C.).

Solvents and solutes can be broadly classified into polar (hydrophilic) and non-polar (lipophilic or hydrophobic). The polarity can be measured as the dielectric constant or the dipole moment of a compound. Polar solvents can be further subdivided into polar protic and polar aprotic solvents. Polar protic solvents contain acidic hydrogen atoms like that in hydroxy (—OH) or amino (—$NH_3$) groups. Water (H—O—H), ethanol ($CH_3$—$CH_2$—OH), or acetic acid ($CH_3$—C(=O)OH) are representative polar protic solvents. Polar solvents, of which water is an example, have molecules whose electric charges are unequally distributed, leaving one end of each molecule more positive than the other. The simplest qualitative definition of a polar solvent is that a polar solvent is one that will dissolve and stabilize dipolar or charged solutes. The polarity of a solvent determines which type of compounds it is able to dissolve and with which other solvents or liquid compounds it is miscible with.

Hygroscopic according to the present invention describes a substance that has the property of readily absorbing moisture from the air.

In a preferred embodiment of the present invention the polar and hygroscopic solvent(s) used in the liquid fill have a dielectric constant of at least 6.0 at 20° C.

In one embodiment the matrix composition of the present invention is a polyhydric alcohol or a polyhydric alcohol derivative particularly those having from 2 carbons. Preferred polyhydric alcohol or a polyhydric alcohol derivative has 2 to 10 carbons and 2 to 10 hydroxyl groups, preferably from 2 to 6 hydroxyl groups. Polyhydric alcohol derivatives are e.g. ethers, esters.

In a preferred embodiment the solvent of the matrix composition is selected from the group consisting of ethylene glycol, propylene glycol (PG), poly ethylene glycol (PEG), glycerol, mannitol, sorbitol, xylitol, inositol, maltitol, lactitol, propylene glycol and mixtures of any of the foregoing. In a more preferred embodiment, the solvent is selected from the group consisting of glycerol, mannitol, sorbitol, xylitol, inositol, maltitol, lactitol, propylene glycol (PG), poly ethylene glycol (PEG) and mixtures of any of the foregoing.

Preferably the solvent is glycerol or a mixture of glycerol and water. Most preferably it is glycerol. Glycerol is a colourless, odourless, hygroscopic and sweet tasting viscous liquid. Glycerol has three hydrophilic alcoholic hydroxyl groups (—OH).

The liquid fill according to the present invention further comprises an active agent or a mixture of active agents wherein the active agent is soluble in said polar and hygroscopic solvent(s). In one embodiment of the present invention is selected from the group consisting of dietary supplements (for example, L-carnitine, L-carnitine acetyl, L-carnitine tartrate, L-carnitine hydrochloride, S-Adenosyl methionine (SAM-e), S-adenosyl methionin tosylate, garlic, and ginseng, etc.), pharmaceuticals (for example, analgesics, anti-inflammatory agents, anti-arrhythmic agents, anti-asthma agents, etc), amino acids (for example, L-Ornithine, L-Arginine, L-Lysine, L-Histidine, L-Aspartic Acid, L-Threonine, L-Serine, L-Glutamic Acid, L-Proline, etc. . . . ) and vitamins (for example, vitamin A, B1, B2, B3, B5, B6, B9, B12, C, D2, D3, E, etc).

In a preferred embodiment of the present invention, the dietary supplement is selected from the group consisting of calcium supplement, mineral supplement (e.g. comprising Mg, Zn, Mn, Su, Se, Fe, Mo), garlic, ginseng, ginkgo biloba, Echinacea purpurea, Echinacea angustifolia, St John's wort, royal jelly, Co-enzyme Q10, artichoke, aloe vera, red clover, carnitine, L-carnitine, L-carnitine acetyl, L-carnitine tartrate, L-carnitine hydrochloride, S-adenosyl L-methionine (SAM-e), S-adenosyl methionine tosylate, glycosamine or salt thereof, and chondroitine. The dietary supplement is preferably selected from L-carnitine, L-carnitine acetyl, L-carnitine tartrate, L-carnitine hydrochloride, and S-Adenosyl methionine (SAM-e) and mixtures of any of the foregoing. More preferably the active agent is L-carnitine or a derivative of carnitine and S-Adenosyl methionine (SAM-e).

One particular group of dietary supplements is selected from the group consisting of calcium supplements, mineral supplements, garlic, ginseng, ginkgo biloba, Echinacea purpurea, Echinacea angustifolia, St John's wort, royal jelly, artichoke, aloe vera, red clover, S-Adenosyl methionine (SAM-e), S-adenosyl methionine tosylate, a combination of glycosamine and chondroitine, and a combination of a salt of glycosamine and chondroitine.

Another particular group of dietary supplements is selected from the group consisting of Carnitine, L-Carnitine, L-Carnitine acetyl, L-Carnitine Tartrate, and L-Carnitine hydrochloride.

It is noted that L-carnitine (L-3-hydroxy-4-aminobutyrobetaine or L-3-hydroxy-4-N-trimethylaminobutanoic acid) is an essential compound for the metabolism of fatty acids. Carnitine can be synthesised de novo in animal cells, but it is believed that most comes from the diet. Its main function is to assist the transport and metabolism of fatty acids in mitochondria, where they are oxidized for energy production. The delivery system filled with a liquid formulation of L-carnitine can be used as dietary supplement delivery system. The compatible container allows improving bioavailability and effectiveness of L-carnitine that is a key player into weight reducing.

In a further preferred embodiment of the present invention, the dietary supplement is selected from herbal extract that can be selected from the group consisting of artichoke, ginkgo biloba, and mushroom.

In a preferred embodiment of the present invention, the vitamin is selected from the group consisting of vitamin A, B1, B2, B3, B5, B6, B9, B12, C, D2, D3, E and mixtures of any of the foregoing.

In a preferred embodiment of the present invention, the active substance can be a pharmaceutical particularly a member selected from the group consisting of analgesics, anti-inflammatory agents, anthelmintics; named also antihelminthics, anti-arrhythmic agents, anti-asthma agents, antibacterial agents, anti-viral agents, anti-coagulants, antidepressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroxines, anti-tussives, anxiolytics, sedatives, hypnotics, neuroleptics, β-blockers, cardiac inotropic agents, corticosteroids, diuretics, anti-parkinsonian agents, gastrointestinal agents, histamine H-receptor antagonists, lipid regulating agents, muscle relaxants, anti-anginal agents, nutritional agents, sex hormones, stimulants, cytokines, peptidomimetics, peptides, proteins, sera, antibodies, vaccines, nucleosides, nucleotides, genetic material, nucleic acids, and mixtures of any of the foregoing.

In a preferred embodiment of the present invention, the amino acid is selected from the group consisting of L-Ornithine, L-Arginine, L-Lysine, L-Histidine, L-Aspartic Acid, L-Threonine, L-Serine, L-Glutamic Acid, L-Proline, L-Tryptophane, L-Alanine, L-Cystine, L-Glycine, L-Valine, L-Methionine, L-lsoleucine, L-Leucine, L-Tyrosine, L-Phenylalanine, L-Cysteine, L-Norieucine, L-glutamine, L-Asparagine, glutathione and mixtures of any of the foregoing. The amino acid is preferably L-Glycine.

A more preferred embodiment of the present invention is a delivery system comprising a hard HPMC capsule and a liquid fill comprising a dietary supplement, like L-carnitine, and glycerol as a solvent. In another also preferred embodiment the liquid fill further comprises water such as in an amount in the range of 0% to 20%. Most preferably these two latter embodiments do not comprise any further ingredients.

The delivery system of the present invention comprises at least a container, a matrix composition and an active agent. The matrix composition and the active agent can be present in the container at the below mentioned amounts when the container is a hard HPMC capsule, the matrix composition is glycerol and the active agent is S-Adenosyl methionine (SAM-e), L-Carnitine L-Tartrate (LCLT) L-Carnitine or mixtures of any of the foregoing.

The delivery system is preferably an oral delivery system.

Examples of Specific Embodiments

Encapsulated liquid fill of S-Adenosyl methionine (SAM-e) and glycerol in a hard HPMC capsule

| SAM-e | 0-700 mg | preferably 400-500 mg |
|---|---|---|
| Glycerol | 200-1000 mg | preferably 500-800 mg |

Encapsulated liquid fill of L-Carnitine L-Tartrate (LCLT) and glycerol in a hard HPMC capsule

| LCLT | 0-700 mg | preferably 300-400 mg |
|---|---|---|
| Glycerol | 200-1000 mg | preferably 500-800 mg |

Encapsulated liquid fill of L-carnitine and glycerol in a hard HPMC capsule

| L-carnitine | 0-700 mg | preferably 300-400 mg |
|---|---|---|
| Glycerol | 200-1000 mg | preferably 500-800 mg |

The liquid fill may optionally contain a colouring agent or mixture thereof that is a pharmaceutically or food acceptable ingredient. The colouring agent may be in the range of from 0% to 4% based upon the weight of the liquid composition. The colouring agent may be selected from the group consisting of azo-, quinophthalone-, triphenylmethane-, xanthene- or indigoid dyes, iron oxides and hydroxides, titanium dioxide natural dyes and mixtures thereof. Further colouring agent examples are patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, clorophyllin, canthaxanthin, caramel, and betanin.

The present invention provides also a process for the preparation of a delivery system comprising the steps of:

a) mixing together under stirring the matrix composition comprising at least one polar and hygroscopic solvent or a mixture of polar and hygroscopic solvents with the active agent or a mixture of active agents wherein the active agent is soluble in said polar and hygroscopic solvent or mixture of polar and hygroscopic solvents;

b) heating of the blend to a temperature not higher than 100° C.;

c) cooling down of the blend to a temperature not lower than 4° C.;

d) filling of the blend into a container wherein said container is a formed body obtained from a film forming composition comprising at least one polysaccharide or polysaccharide derivative; and e) optionally sealing of the container.

The container is filled up by any usual method well known in the art for example, as described in "Pharmaceutical capsules", second edition, from Fridrun Podczeck and Brian E Jones et al, pages 178-182.

The present invention will now be explained in detail with reference to the examples but it is to be noted that the present invention is not limited thereto.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C. unless otherwise indicated. The amounts of the components are in weight percents based on the standard described; if no other standard is described then the total weight of the composition is to be inferred. It will be understood that numerous additional formulations can be prepared without departing from the spirit and scope of the present invention. The term comprising is understood to include consisting of and consisting essentially of.

Example 1

Example of Liquid Fill

| Component name | Weight | mg/caps |
| --- | --- | --- |
| L-Carnithine pure | 2,842 Kg | 300 |
| Glycerin 98%, pharma grade | 6,158 Kg | 650 |
| Total | | 950 |

Glycerol (liquid form) and L-carnitine (powder form) are weighed and mixed together under stirring from 300 rpm to 500 rpm. Then the composition is heated to 60° C. until the blend is completely solubilised. The blend is cooled down to 40° C. The blend is further stirred from 100 rpm to 300 rpm at 40° C. Finally, the composition rests 72 hours at room temperature under nitrogen. The liquid fill is then encapsulated into hard HPMC capsule, using standard method. The capsules are finally sealed by liquid sealing technology using hydro alcoholic solution.

Example 2

| Component name | Weight | mg/caps |
| --- | --- | --- |
| L-Carnithine-Tartare | 1,905 Kg | 400,00 |
| Glycerol | 3,095 Kg | 650,00 |
| Total | | 1050,00 |

Glycerol (liquid form) and L-carnitine (powder form) are weighed and mixed together under stirring from 300 rpm to 500 rpm. Then the composition is heated to 60° C. until the blend is completely solubilised. The blend is cooled down to 40° C. The blend is further stirred from 100 rpm to 300 rpm at 40° C. Finally, the composition rests 72 hours at room temperature under nitrogen. The liquid fill is then encapsulated into hard HPMC capsule, using standard method. The capsules are finally sealed by liquid sealing technology using hydro alcoholic solution.

Example 3

| Component name | Weight | mg/caps |
| --- | --- | --- |
| S-Adenosyl methionine p-Tosylate (SAME), | 3,333 Kg | 350,00 |
| Glycerol | 6,667 Kg | 700,00 |
| Total | | 1050,00 |

Glycerol (liquid form) and S-Adenosyl methionine p-Tosylate (SAME) (powder form) are weighed and mixed together under stirring from 300 rpm to 500 rpm. Then the composition is heated to 60° C. until the blend is completely solubilised. The blend is cooled down to 40° C. The blend is further stirred from 100 rpm to 300 rpm at 40° C. Finally, the composition rests 72 hours at room temperature under nitrogen. The liquid fill is then encapsulated into hard HPMC capsule, using standard method. The capsules are finally sealed by liquid sealing technology using hydro alcoholic solution.

Compatibility Test:

Main objective of the Test is to evaluate the storage stability of HPMC hard capsules filled with L-carnitine, L-carnitine L-tartare, or S-Adenosyl methionine p-Tosylate. The mechanical (brittle fracture, disintegration), chemical (water exchange) properties are investigated.

Implementation of the Test

Prepare the liquid fill as in Examples 1 to 3 above.

Encapsulate each of the above formulations (Examples 1-3) into a hard HPMC capsule.

Seal the filled hard HPMC capsules by liquid sealing technology using hydro alcoholic solution.

Store the filled hard HPMC capsule in a moist environment of 2.5% and 10% corresponding to dry storage condition, 65% and 75% corresponding to humid storage condition. Moist environment of 30% to 50% correspond to normal storage conditions.

Measure the weight changes, assess external aspect, and measure disintegration rate. The weight of the capsules tested is measured on precision scale. The assessment of the external aspect of the tested capsules is made by visual assessment. The capsule disintegration is measured within a prescribed time wherein the capsule is placed in a liquid medium at experimental condition as disclosed in the European Pharmacopoeia 07/2005: 0016 and 01/2006:20901 (2.9.1).

Performance Test Results

TABLE 1

| Active agent | Water exchange (after 2 weeks) at | | Broken capsules (after 3 weeks) at (% water) | | Disintegration (after 3 weeks) at 40° C. 75% RH |
| --- | --- | --- | --- | --- | --- |
| | 2.5% RH | 65% RH | 2.5% RH | 10% RH | |
| L-Carnitine | 0.69% | 33.65% | 8% | 2% | <7 min |
| S-Adenosyl methionine p Tosylate | −0.2% | 19.6% | 6% | 0% | <8 min |
| L-Carnitine L-Tartrate | −1.0% | 21.5% | 2% | 6% | <8 min |

The sign "−" means a loss of water.
No sign means a gain of water.
RH means Relative Humidity.

Water exchange column relates to the moisture exchange between encapsulated formulation and capsule shell under various conditions of relative humidity (2.5% and 65%). A hygroscopic material when filled into the capsule could extract moisture from the shell thereby inducing embrittlement or migrate into the shell and thereby weaken it. The results show that the water exchange is almost nonexistent at a RH of 2.5%. Further capsules are accepted as long as no visual deformation is observed after storage at 2.5% RH and 35% RH that is presently the case.

Broken capsules column relates to the effect of moisture exchange between liquid fill and hard HPMC capsule under dry storage condition (2.5% and 10% RH). Capsules are considered compatible when broken capsules do not exceed 30% of the total of capsules tested at 2.5% RH. The results show that the amount of broken capsules is never higher than 8%.

It should be noted that when the moisture content in the hard HPMC capsule shell decreases below 1%, the capsules can break easily.

The disintegration column relates to the disintegration rate of hard HPMC capsule under specific storage condition. The disintegration properties are, mostly, based upon the ability of the container to swell in the presence of a fluid, such as water or gastric juice. This swelling disrupts the continuity of the capsule structure and thus, allows the different components to enter into solution or into suspension. The disintegration rate refers to how fast a capsule dissolves in solvent.

Capsules are considered compatible when disintegration time is less than 45 minutes as per Pharmacopoeia method.

Stability Test

Main objective of the Test is to evaluate the storage stability of HPMC hard capsule filled with L-Carnitine, L-Carnitine L-Tartare, and SAM-e.

Test Procedure

Prepare liquid fill as in Examples 1 to 3 above.

Encapsulate the above formulations into hard HPMC capsule.

Seal hard HPMC capsule by liquid sealing technology using hydro alcoholic solution.

Store the filled hard HPMC capsule at room moist conditions.

Assessment of stability properties using European Pharmacopoeia 01/2005:1339 for L-Carnitine and L-Carnitine L-Tartare and HPLC dosage method for SAM-e.

The dosage by HPLC is done by solubilising reference SAM-e into 0.0001 M HCl solution. Tested capsules are opened and content is solubilised into 0.0001 M HCl solution. SAM-e reference and tested are detected at 254 nm on HPLC using a methanol aqueous buffer 60/40 VN. Amount of SAM-e is calculated for all samples and compared with each other.

Performance Tests Results

| Active agent | Method | Results |
| --- | --- | --- |
| SAM-e | HPLC Dosage | Stability confirmed after 1 year at room conditions and ongoing |
| L-Carnitine L-Tartrate | EP method | Stability confirmed after 1 year at room conditions and ongoing |
| L-Carnitine | EP method | Confirmed after 1 month at 40° C./75% RH |

EP method: European Pharmacopoeia 01/2005: 1339
RH means Relative Humidity.

Results show globally that liquid filled hard HPMC capsules are stable and can be stored at room temperature.

The test results from the Examples described above show that the container of the present invention is tolerant to and compatible with polar and hygroscopic solvents. Further, the active agent is stable in and compatible with the matrix composition and the container. Finally it has been observed that the active agent is highly soluble in the matrix composition.

What is claimed is:

1. A delivery system comprising: (a) a hard capsule comprising hydroxypropylmethyl cellulose (HPMC); (b) a liquid fill comprising at least one solvent which is both polar and hygroscopic or a mixture of solvents each of which is both polar and hygroscopic, wherein at least one solvent is glycerol; and (c) an active agent or a mixture of active agents, wherein the active agent is solubilized in said polar and hygroscopic solvent or mixture of polar and hygroscopic solvents.

2. The delivery system according to claim 1, wherein the system further comprises water.

3. The delivery system according to claim 1, further comprising at least one coating.

4. The delivery system according to claim 1, wherein the active agent is selected from the group consisting of dietary supplements, pharmaceuticals, amino acids, vitamins, and herbals.

5. The delivery system according to claim 4, wherein the dietary supplement is selected from the group consisting of calcium supplements, mineral supplements, garlic, ginseng, ginkgo biloba, Echinacea purpurea, Echinacea angustifolia, St John's wort, royal jelly, artichoke, aloe vera, red clover, Carnitine, L-Carnitine, L-Carnitine acetyl, L-Carnitine Tartrate, L-Carnitine hydrochloride, S-Adenosyl methionine (SAM-e), S-adenosyl methionin tosylate, a combination of glycosamine and chondroitine, and a combination of a salt of glycosamine and chondroitine.

6. The delivery system according to claim 1, wherein the liquid fill further optionally comprises at least one coloring agent in an amount ranging from about 0% to about 10% based upon the weight of the liquid.

7. The delivery system according to claim 5, further comprising at least one coating.

\* \* \* \* \*